United States Patent [19]

Petersen et al.

[11] 4,305,300
[45] Dec. 15, 1981

[54] RAILWAY CAR SIDE FRAME TEST MACHINE

[75] Inventors: Paul S. Petersen; Fred S. Tsuchiya, both of Minnetonka, Minn.

[73] Assignee: MTS Systems Corporation, Eden Prairie, Minn.

[21] Appl. No.: 144,616

[22] Filed: Apr. 28, 1980

[51] Int. Cl.³ .............................................. G01N 3/00
[52] U.S. Cl. ...................................... 73/788; 73/794; 73/806
[58] Field of Search ................. 73/788, 794, 795, 798, 73/806, 808, 816, 669

[56] References Cited

U.S. PATENT DOCUMENTS

| | | | |
|---|---|---|---|
| 2,431,295 | 11/1947 | Eksergian et al. ...................... | 73/795 |
| 3,135,106 | 6/1964 | Lazan ..................................... | 73/794 |
| 3,229,510 | 1/1966 | Bodemeijer ........................... | 73/761 |
| 3,257,844 | 6/1966 | Shaver ................................... | 73/794 |
| 3,555,893 | 1/1971 | Holzman ............................... | 73/669 |
| 3,581,560 | 6/1971 | Odier ..................................... | 73/117 |
| 3,713,330 | 1/1973 | Lentz .................................... | 73/798 |
| 3,718,040 | 2/1973 | Freeman et al. ...................... | 73/146 |

OTHER PUBLICATIONS

"Symington Side Frame Testing Machine", Symington-Gould Corporation, Rochester & Depew, N.Y., pp. 1-15.

American Steel Foundries Side Frame Tester, (3 pages), 1/19/72.

"Summary of Truck Side Frame Fatigue Test Machine History and Loadings", Dresser Transportation Equipment Division, Dresser Industries, Inc., 1/72, (3 pages).

*Primary Examiner*—Anthony V. Ciarlante
*Attorney, Agent, or Firm*—Kinney, Lange, Braddock, Westman and Fairbairn

[57] ABSTRACT

A railroad side frame test machine for loading side frames used on the trucks or carriages for railway cars to simulate the in-use loads utilizing a compact linkage that provides for direct loading of the specimen in the various load directions. The forces are applied to the specimen to insure that certain reactions are grounded, while other applied forces are basically ungrounded to effectively eliminate "cross talk" between the various input loads or forces.

17 Claims, 10 Drawing Figures

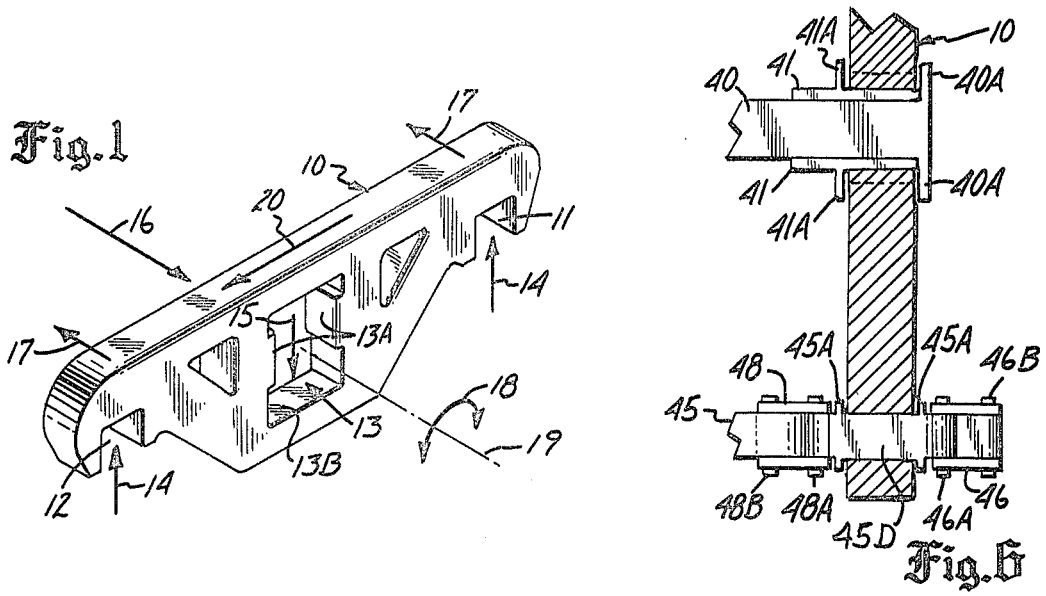
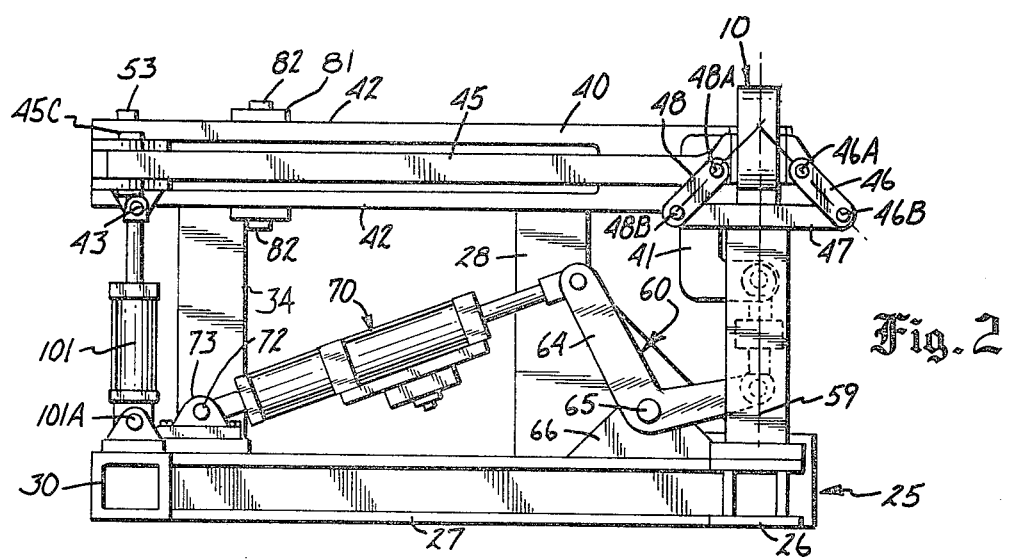
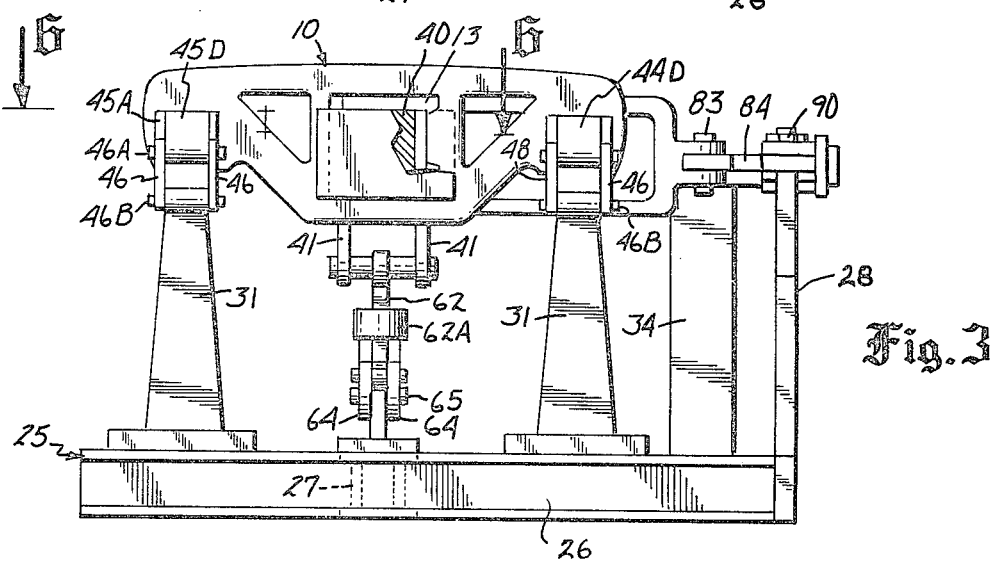

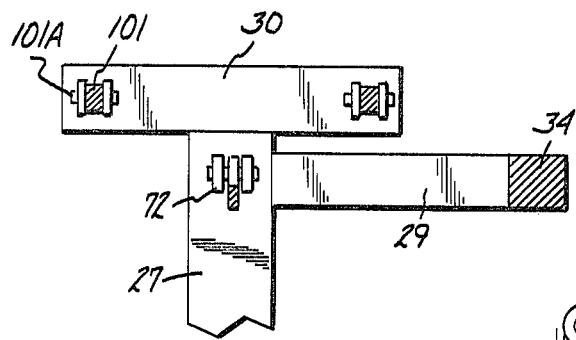
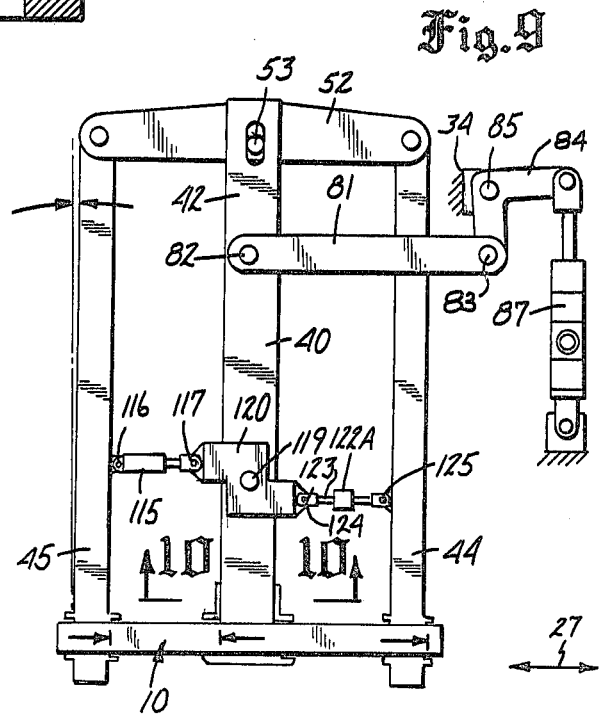
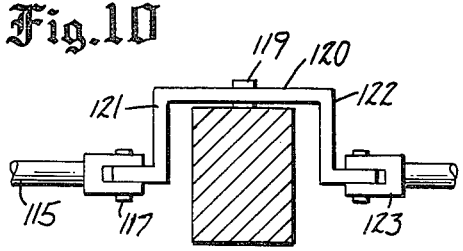
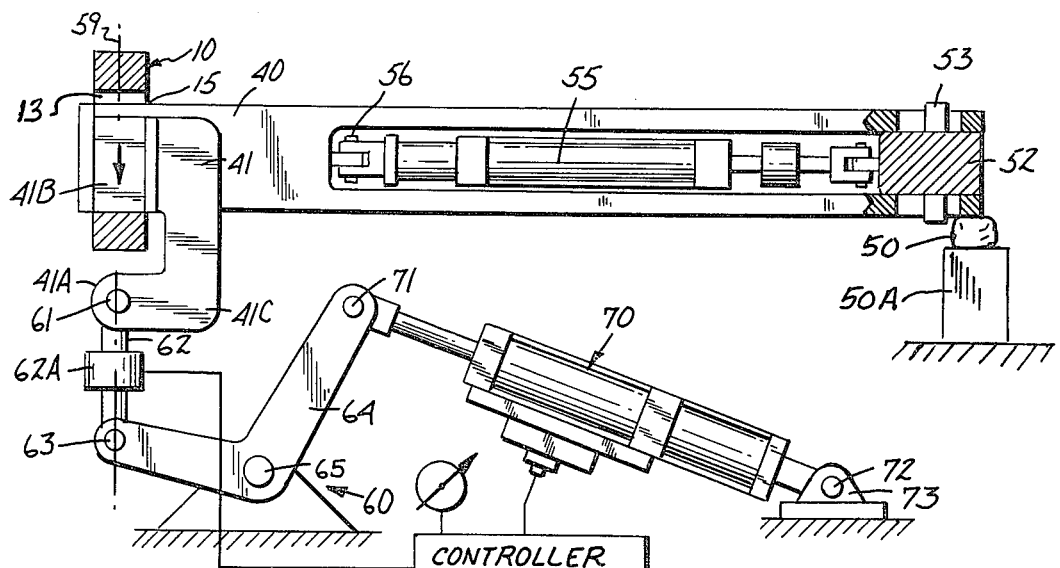

RAILWAY CAR SIDE FRAME TEST MACHINE

BACKGROUND OF THE INVENTION

1. The present invention relates to testing apparatus particularly adapted for use with side frames of trucks for railway cars.

2. Prior Art

In the prior art the desirability of testing side frames of railroad cars has long been known. The "Symington" Side Frame Testing Machine has been used for many years, and comprises a very large complex machine that does in fact include loadings in several directions including vertical, transverse, center twist, longitudinal, end twist, center impact and end impact. The loads can be cycled as they are applied and the side frames are primarily loaded in the Symington machine through complex spring and linkage arrangements. Further, the force applying mechanisms are made so that there is a substantial amount of cross talk between the individual forces being applied which makes it hard to control the tests accurately.

Another type of fatigue tester for railway side frames is made by the American Steel Foundries Company.

In the patented art, U.S. Pat. No. 3,718,040 illustrates a Method and Apparatus For Evaluating Railroad Track Structure And Car Performance utilizing the axles and wheels of the railroad car mounted in the side frames that are illustrated in that patent. The patent deals with measuring the actual forces during use, as a means of disclosing track condition changes between different runs with the same side frame assembly.

U.S. Pat. No. 3,257,844 illustrates an apparatus for testing the sills of cushion cars wherein the entire railroad car is loaded in a desired manner, and U.S. Pat. No. 2,431,295 also illustrates a device for loading an entire car relative to rails for testing various components of a railway car.

U.S. Pat. No. 3,135,106 shows a Static-Dynamic Fatigue-Creep Testing Apparatus that utilizes a type of a C shaped spring for loading in one direction. U.S. Pat. No. 3,713,330 also shows a type of device for loading an axle in three different axes, utilizing bell crank arrangements for keeping the unit compact, and also includes servo controlled cylinders for loading.

Additional patents which show fatigue or other testing for vehicle components include U.S. Pat. No. 3,229,510 which tests apparatus for ball screws and ball driven actuators; U.S. Pat. No. 3,581,560 which provides a stationary test stand for vehicles; and U.S. Pat. No. 3,555,893 which simulates lateral and steering forces on an automobile frame.

SUMMARY OF THE INVENTION

A railway side frame tester including a static (main) frame which permits loading the side frame vertically, and transversely (horizontally side to side with respect to the rails of a railroad track) without having any substantial cross talk between the force inputs.

It should be noted that railway side frames are held together with cross bolsters which are generally spring mounted in openings in the side frame, and the axles themselves or the wheels are held in axle "nests" in the bottom side of the side frame. Additional loading such as center twist and twist and longitudinal can also be added in a compact loading assembly. By maintaining the various inputs isolated from each other, proper control of the load and the testing sequence can be achieved.

BRIEF DESCRIPTION OF THE DRAWINGS

FIG. 1 is a perspective view of a typical railway car side frame which is being tested with the present invention;

FIG. 2 is a side elevational view of a testing apparatus made according to the present invention having a side frame installed thereon;

FIG. 3 is an end view of the device of FIG. 2 as viewed from the right end thereof;

FIG. 6 is a fragmentary sectional view taken as on line 6—6 in FIG. 3;

FIG. 7 is a part schematic side sectional view showing the vertical loading links;

FIG. 8 is a top view of the rear portions of the frame of FIG. 4 with parts broken away;

FIG. 9 is a schematic top plan view of the test apparatus used for applying a center twist load and longitudinal load; and FIG. 10 is a sectional view taken as on line 10—10 in FIG. 9.

DESCRIPTION OF THE PREFERRED EMBODIMENT

Figure 4:
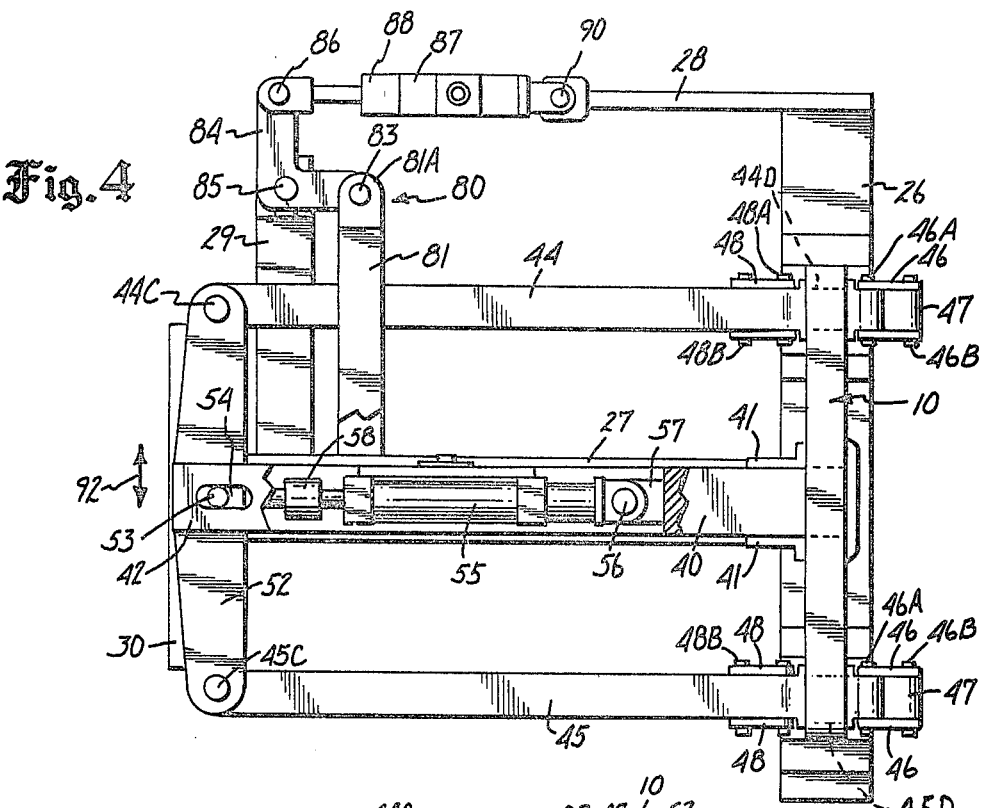
FIG. 4 is a top plan view of the device of FIG. 2.

A railway truck side frame illustrated generally at 10 which is to be tested includes a pair of longitudinally spaced axle nests or saddles 11 and 12 at opposite ends thereof and a bolster support journal and spring mount opening indicated generally at 13 through which a cross bolster (not shown in FIG. 1) of a railway car extends. The bolster is the member which is fixed to the car body. The railway wheels and axles mount in the axle nests or saddles 11 and 12, and the bolster holds the side frame 10 on both sides of the railway car in position and reacts loads applied between the car and the axle nests as the train moves along the track. The car side frame opening 13 includes bolster ways 13A near the top of the opening 13 to guide and support the bolster. The lower plate 13B carries springs which transfer vertical loads from the wheels and side frame to the bolster.

In general, there are three primary forces acting on the railway side frame. First, there are vertical inputs at the axle nests 11 as indicated by the arrows 14, which in turn are reacted through the spring plate 13B and springs to the bolster which reacts the load with a force indicated by the arrow 15 in FIG. 1.

Also, a transverse input, that is, transverse to the central, longitudinal plane of the side frame, is reacted through the bolster mounting. The transverse input is represented by the side loading force indicated by arrow 16 and reacted at the axle nests as indicated by the arrows 17.

Additionally, there is a center twist that tends to twist the side frame about its mounting at the bolster opening 13. This twist force is a moment or couple caused by unequal lateral forces at the respective axle nests. In other words, the forces that were represented by arrows 17 are at many times unequal in a railway side frame causing the twisting of the frame 20 which has to be reacted at the bolster.

Additional forces that load a railway side frame, but which are not as prevalent, include an end twist as indicated by the arrow 18 in FIG. 1 tending to twist the side frame about its mounting bolster and thus about its central axis indicated at 19. The twist is caused by unequal vertical forces at the axles. That is, the forces represented by arrows 14 are unequal. Further, there is longitudinal loading on the side frames, that is in the direction that is indicated by the arrow 20. Longitudinal loading comes about primarily through braking loads applied to the wheels and axles and reacted through the side frames.

The test frame assembly 25 supports the various actuators and linkages needed to test the side frames. The test frame assembly includes a main cross beam 26 which extends in the longitudinal direction of a side frame 10 which is mounted in the test frame (see FIGS. 3 and 4) and a backbone beam 27 (see FIGS. 2 and 4) that is welded into the beam 26 to form a "T". The two main support beams 26 and 27 are used for supporting other frame portions including an upright brace 28 at one side of the frame, and a cross frame member 29 that extends generally parallel to frame member 26 and is spaced therefrom. Frame member 29 is fixed to the backbone beam 27. The frame member 29 and beams 26 and 27 rest on a supporting surface.

Adjacent to the frame member 29 and spaced slightly therefrom along backbone beam 27 there is a short actuator support beam 30 welded to the end of the backbone beam 27. The support beam 30 extends laterally from the backbone beam 27.

The frame assembly 25 further includes a pair of upright pedestals 31,31 fixed to the upper surface of the main cross beam 26, and as will be explained the upright pedestals 31,31 are used for supporting the linkages that in turn support the side frame for testing through the nests or saddles for mounting the axles in a side frame 10.

Figure 5:
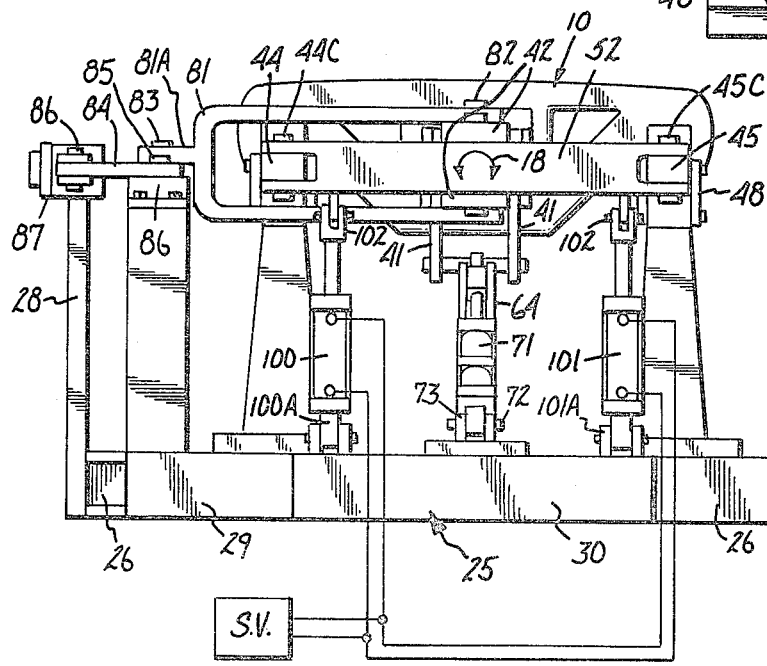
FIG. 5 is an end view of the device of FIG. 2 viewed from the opposite end from FIG. 3.

The member 29 has an upright support column 34 fixed thereto that is used for testing and loading components. It should be noted that the upright brace 28 extends along one side of the machine as shown in FIG. 3, 4 and 5.

To mount the side frame 10 to be tested onto the test frame 25 an elongated bolster or beam 40 is mounted through the center bolster support opening 13 of the side frame. The bolster has retainer flanges, as shown in FIG. 6 that are on opposite sides of the side frame 10. These flanges indicated at 40A on the exterior of the bolster can be formed in any desired manner and can be bolted in place or made removable in some other way if desired to permit installation of a side frame for testing. The flanges 41A, 41A on the opposite side of the frame 10 from the flanges 40A are formed on the sides of a pair of loading C shaped members 41,41 on opposite sides of the bolster 40, which will be more fully explained.

The bolster is bifurcated at its other end, as will be explained, and is used for mounting the transverse loading actuator. The open part of the bolster comprises upper and lower plates 42, which are spaced apart and extend generally perpendicular to the plane of the side frame being tested. The lower plate 42 is pivotally mounted about a generally horizontal pivot axis 43, which is also parallel to the plane of the side frame, and perpendicular to the longitudinal axis of the bolster. The plane of the side frame when a side frame is mounted on the test frame coincides (at rest) with the primary loading plane of the test frame, which is the vertical plane. The pivot axis 43 is formed by support pins of a pair of actuators that support a cross member 52 mounted between the plates 42, as will be explained.

Thus the bolster 40 can pivot about axis 43 so that as the side frame is loaded up or down, the bolster 40 is not loaded in bending. The flanges 40A and 41A are spaced from the frame 10 slightly so that the bolster and the side frame can move relative to each other a limited amount. The opening 13 has the pads 13A which fit tightly, but slidably, on the sides of bracket 41 and thus hold the bolster snugly for loading. The surfaces around the edges of opening 13 transfer or carry the loads.

The side frame 10 is further mounted to a pair of elongated links indicated at 44 and 45 which simulate the mounting of the cross axles normally mounted in the axle nests 11 and 12, respectively, of the side frame. The links 44 and 45 as shown in FIG. 6 have hub members 44D and 45D integral therewith which fit in the axle nests of a frame 10. Flanges 44A and 45A are formed on the hub members on opposite sides of the side frame 10 in the same manner as the flanges 40A and 41 of the bolster, to keep the amount of movement in direction along the longitudinal axes of the hubs and links to a minimum. The hub members of the links in turn are each mounted at their ends adjacent to the flanges 44A and 45A through separate four bar linkages to the upright columns or pedestals 31. As shown in FIG. 2 typically, the four bar linkage for the hub member 45D of the elongated link 45 includes a link 46 (which comprises a pair of straps on opposite sides of the hub member 45D of the link 45). The straps forming link 46 are pivotally mounted as 46A to the hub member 45D and as at 46B to a plate 47 that is mounted on the top of the respective pedestal 31.

Additionally a link 48 formed as a pair of straps (which act as a single link as well) are pivotally mounted as at 48A to the hub 45D and as at 48B to the opposite end of the support plate 47.

The hub member 44D of link 44 is also mounted with a pair of pivoting links 47 and 48, each link being formed of a pair of straps pivotally connected to the aligned plate 47 and to the hub 44D at opposite ends thereof.

The four bar linkage for the hub members 44D and 45D, respectively, each include the link 46 and the link 48, the respective plate 47, and the respective hub member itself. The plates 47, which are fixed to the pedestals 31, and thus to the frame assembly 25, form the fixed link or bar of each four bar linkage.

The elongated links 44 and 45, respectively, extend parallel to the bolster 40, and as shown are on opposite sides of the bolster (see FIG. 4). The ends of the elongated links 44 and 45 opposite from the side frame 10 are each pivotally mounted as at 44C and 45C, respectively, to the opposite ends of an equalizer or "evener" beam indicated at 52. The equalizer or evener beam 52 extends between the outer ends of links 44 and 45 and is generally parallel to the side frame 10. The evener beam 52 is positioned between the upper and lower plates 42 of the bolster, and a vertical pin 53, which is slidably guided in slots 54 in the upper and lower plates 42 of the bolster, forms a pivot for the evener beam 52.

The transverse or side loading on the test side frame is achieved by placing tension or compression loads axially along the elongated links 44 and 45. This load is then reacted by the center bolster. It should again be noted that the hub end portions of the elongated links 44 and 45 at the side frame 10 are mounted in the axle nests of the side frame and are restrained from axial movement relative to the side frame being tested by flanges or ledges, and are also guided by the four bar linkage arrangements previously described. In order to load the equalizer or evener beam, a servo controlled hydraulic actuator 55 is mounted as at 56 (see FIG. 4) to a support 57 positioned between the upper and lower plates 42 of the bolster, and the rod of the actuator 55 is connected through a load cell 58 to the pin 53, which in turn causes the evener beam 52 to be loaded along the axis of the bolster when the actuator 55 is extended and retracted. The pin 53 is permitted to slide in slots 54 for loading.

The actuator 55 thus is positioned between the upper and lower plates 42 in the bolster 40 and the forces that are placed when actuator 55 is operated are reacted to the bolster or beam 40 in an opposite direction from the axial forces on the elongated links 44 and 45 (loading the side frame in lateral direction), thereby tending to cause the side frame to bow. This loading is also lateral to the vertical, primary loading plane of the test frame. The equalizer beam 52 causes a substantially equal load to be placed into the elongated links 44 and 45 so that the axle nests of the test side frame will carry this load and react it through the center part of the test side frame 10 and the bolster.

The elongated links 44 and 45 and the connected hub members 44D and 45D thus apply the transverse input load on the side frame that is represented by arrows 16 and 17 in FIG. 1.

The vertical inputs represented by the arrows 14 and 15 in FIG. 1 also are reacted through the elongated hubs 44D and 45D and the four bar linkages comprising the hub members and pivoting links 46 and 48, back to the plates 47 and pedestals 31. This is done by loading the bolster or beam 40 in vertical direction or in other words parallel to the plane of the side frame, which is the primary loading plane for a test side frame. The members 41 on opposite sides of the bolster 40, as shown in FIG. 7 schematically are of a general "C" shape. The placement of the members 41 along the sides of the bolster 40 is such that top leg 41B of the "C" member 41 extends into the opening 13 and is fixed to the bolster symmetrically about the center plane 59 of the side frame, as for example by welding. The vertical leg 41C of member 41 is not fixed to the bolster. The lower leg 41A of each member 41 is positioned directly below the side frame 10.

The members 41 and thus the bolster 40 are loaded along the primary loading plane through a loading assembly indicated generally at 60 which includes a loading pin 61 passing through the leg 41A and a loading link 62. The pin 61 has an axis that lies along the center dividing plane 59 of the side frame, which also is the primary loading plane. This means that vertical loads applied along plane 59 will also be reacted to the side frame 10 along this plane. The loading will be symmetrical on opposite side of plane 59 because the legs 41B are the only parts attached to the bolster.

The link 62 has an opposite end mounted with a pin 63 to one end of a bell crank assembly 64. The bell crank assembly is shown in FIG. 7 schematically, and also is shown in FIG. 2 for example. The bell crank assembly 64 is pivotally mounted on a pin 65 to a support ear 66 that is fixed to the upper member of the backbone 27 (see FIG. 2). The loading arm of the bell crank is connected to an actuator 70 which is a conventional servo controlled actuator, and the rod end of the actuator 70 is connected with a pin 71 to the opposite end of the bell crank 64 from the pin 63. The base end of the actuator 70 is connected with a pin 72 to an ear or support 73 also mounted onto the backbone 27, but at an opposite end of the backbone 27 from the side frame 10 as shown in FIG. 2.

The link 62 has a load cell 62A in it so that the vertical load along the plane 59 can be measured. The bell crank 64 is oriented so that the arm connected to link 62 is substantially perpendicular to plane 59. The movement of the bell crank is not substantial during loading, so the arcurate movement of the loading arm of the bell crank 64 does not adversely affect the loading.

As shown schematically in FIG. 7, when the actuator 70 is extended, the bell crank 64 will pivot about its bell crank pivot 65, causing a tension in the link 62. This tension load will be measured by the load cell 62A for control purposes (the actuator 70 is servovalve controlled), and the tension load also then will load the bolster 40 downwardly. The bolster 40 is free to move slightly relative to side frame 10 in direction along the plane 59 of the side frame 10, but when the bolster rests on the bottom of opening 13 the bolster will load the frame 10. The bolster pivots about its support on pins 102, as will be explained. The vertical loading is a downward force as indicated by the arrow 15 on the side frame 10 (FIG. 1), and the force is reacted at the axle saddles or nests 11 and 12 as indicated by the arrow 14 in FIG. 1. These axle nest reactions therefore are transmitted from the side frame 10 to the hub members 44D and 45D of the elongated links 44 and 45, to the respective links 46 and 48 and through plates 47 to the pedestals 34.

The side frames 10 are not generally loaded upwardly because the downward force simulates the weight of the railroad car acting through the support springs used. Thus the loads applied by C frames 41 are cycled from high to low or to zero, but are not reversed. If desired, however, the hubs can have means for restraining some upward movement of the side frame being tested.

Another major input for the side frame testing machine is the center twist input which tends to place a twist in the test side frame 10 about an axis lying in the center plane 59 of the side frame and generally perpendicular to the plane in which the elongated links 44 and 45 lie. This is basically a twist load about a central vertical axis of the side frame 10. The twist loading is applied by moving the bolster 40 and the elongated links 44 and 45 from side to side in a parallelogram. The ledges 40 and 41 of the bolster do the loading onto this test side frame and the reaction is through the axle nests, elongated links 44 and 45 and through the four bar linkages, including the hub members 44D and 45D.

Referring specifically to FIGS. 2, 4 and 5, the center twist input actuating mechanism is indicated generally at 80. A bifurcated yoke 81 is pivotally mounted on suitable short pins to the upper and lower plates 42 of the bolster. These pins are indicated at 82 in FIG. 2 for example. In FIG. 4 one of the legs of the bifurcated yoke 81 is broken away adjacent to the bolster, and the legs of the yoke also are spaced over and straddle the elongated link 44 as shown in FIGS. 4 and 5. The yoke 81 has a connector tang 81A which is pivotally mounted as at 83 to one leg of a bell crank loader 84. The bell crank loader in turn is pivotally mounted with a pivot pin 85 to a bracket 86 mounted on the top of the pedestal 34, which in turn is part of the load frame assembly 25. The opposite end of the bell crank 84 is coupled with a pivot pin 86 to the rod end of an actuator 87. The rod of the actuator 87 has a load cell 88 therein to measure the load applied by the actuator.

The base of the actuator 87 is connected with a pin 90 and a suitable connector mounted on the brace or member 28. Thus by moving the actuator 87 to extend and retract the rod, the pin 86 will cause the bell crank 84 to pivot about its pivot pin 85 placing tension and compression load in the yoke 81. This in turn will cause the bolster 40 to tend to pivot from side to side relative to the test side frame 10 so that the outer or remote end of the bolster will move transversely to its longitudinal axis. As previously explained, the evener beam 52 used for loading the elongated links 44 and 45 is mounted with a pin 53 in a slot 54 on the plates 42 of the bolster and the movement of the bolster will cause the evener bar to move transversely as generally indicated by the arrow 92 in FIG. 4. This will tend to skew the evener beam 52 causing the elongated links 44 and 45 to skew as well as restrained by the four bar linkages at the respective axle nests. The four bar linkage permits the elongated links 44 and 45 to move longitudinally or axially, and this permits the links 44 and 45 to skew while the ends of the side frame 10 are restrained by flanges 44A and 45A. The elongated links 44 and 45 and evener beam 52 "parallelogram" relative to the test side frame 10 and the bolster 40 pivots in the test side frame with diagonally oriented retainer flanges 40A and 41A bearing against opposite corners of the side frame at bolster opening 13 of the test side frame, putting a twist into such side frame. The four bar linkages carry the reactive forces back to the test frame to ground the reactions back to the test frame through the flanges on elongated links 44 and 45.

The parallelograming of the elongated links 44 and 45 and the evener beam 52 causes the twist loads to be put in about a central vertical axis lying in the center plane of the side frame 10.

In addition to loading as previously described, the apparatus of the present invention may include a device for applying a load called "end twist" into the test side frame 10 which is accomplished by twisting the bolster 40 about its longitudinal axis. The actuators for loading the bolster for end twist are shown perhaps best in FIG. 5. First and second actuators 100 and 101 are respectively mounted at their base ends as at 100A and 101A to the cross beam 30. The rod ends of these actuators 100 and 101 are mounted as indicated at 102 to the opposite ends of the evener beam 52. Because the evener beam 52 in turn is connected through the pin 53 to the plates 42 of the bolster, the operation of the actuators 100 and 101 in opposite directions simultaneously (one actuator retracts as the other extends) will cause the evener beam or equalizer 52 to be twisted about the longitudinal axis of the bolster as indicated by the arrows 18 in FIGS. 1 and 5.

It should be noted that the actuators 100 and 101 are preferably cross ported so that upon actuation, the fluid under pressure that is supplied through suitable servo-valves will cause one of the actuators to retract while the other one extends, and vice versa. By suitable servo controls the amount of the end twist being loaded into the side frame can be quite closely controlled. Again, the four bar linkages including links 46 and 48 control the movement of the hub members 44D and 45D and the elongated links 44 and 45 so that the twist did not adversely affect other movements or loadings on the test side frame.

Note that the load is applied in downward direction on the axle nests of the side frame. The mountings of the hub members 44D and 45D and their axle nests do not resist a substantial upward movement of the side frame. Thus the center twist loading alternates between the bolster and one axle nest and then to the other axle nest. The vertical loading through members 41 and actuator 70 resists the tendency of the bolster and side frame being tested to lift.

Longitudinal loading can be applied onto a side frame 10 mounted on the test frame through actuators coupled between the elongated links 44 and 45 and the bolster to tend to cause the elongated links 44 and 45 to move in longitudinal direction of the side frame being tested relative to the bolster. For sake of clarity, the actuators and links for this loading have not been shown in FIGS. 1 through 8, and a general schematic showing of the arrangement is made in FIGS. 9 and 10. The center twist actuator is also schematically shown in these figures. Only one very short hydraulic actuator is necessary, as shown, but two actuators can be utilized for longitudinal loading.

An actuator 115 is mounted as at 116 to an ear or tab on the elongated link 45, and the rod end of the actuator 115 is connected as at 117 to a loading lever assembly indicated at 120 that is pivotally mounted as at 119 along an axis that is perpendicular to the longitudinal axis of the bolster 40 and parallel to the plane of the side frame 10. The loading lever 120 is made so that it has depending legs on opposite sides of the bolster as indicated at 121 and 122 in FIG. 10 so the actuator 115 may act on the lever along the plane defined by the center axes of elongated links 44 and 45.

The leg 122 has an ear to which a reaction link 123 is connected as at 124. The link 123 can carry both tension and compression and has its opposite end connected as at 125 to an ear mounted on a link 44. The link 123 as shown includes a load cell shown at 122A so that the load applied by the actuator 115 can be measured and controlled.

It can be seen that upon extending the actuator 115, the lever 120 will pivot about its mounting pivot pin 119 in a first direction, and this will cause a force to be reacted through the link 123 to the elongated link 44. Opposite movement of the actuator 115 will cause an opposite reaction in the link 123 and again thus to link 44. When the actuator 115 is extended the link 45 is loaded to move away from the bolster while elongated link 44 is pulled toward the bolster. This is reversed when the actuator 115 is retracted the loading is reversed. The loading occurs in use when brakes are applied.

By running the actuator 115 in the desired manner, the reaction from elongated links 44 and 45 will be applied to the side frame 10 through the bearing seats. The pivots for the links 46 and 48 which hold the hubs 44D and 45D to the pedestal can be made to accommodate the slight movement necessary for loading the railway car side frame in its longitudinal direction. The beam 52 also reacts these loads.

Thus in a unitary side frame test machine, all of the necessary loading directions can be accommodated quite easily to permit individual forces to be applied to a side frame for fatigue testing.

One of the features of the arrangement just described is that the side frame is grounded to the static test frame 25 by the four bar linkages comprising the links 46 and 48 holding hubs 44D and 45D to the pedestal 31.

The links 46 and 48 provide a kinematic center point in space at each axle nest which is the reaction point for loads applied to these links. The point lies at the intersection of the line passing through the pivots of the links, as shown in FIG. 2. This point lies on the center plane of the side frame. The point is rotationally free. The kinematic point is the instantaneous center of the four bar linkages used at each of the hubs 44D and 45D. Further, by using the vertical loading link beneath the side frame attached through the C frame linkage that causes the force in vertical direction to be applied along the vertical bisecting plane of the side frame 10, the tendency of the linkage to apply other than a pure vertical load is avoided. No twisting load is introduced by the vertical actuator.

The transverse input is from an actuator centered within the bolster, and connected to the evener beam 52 which splits the transverse load into two equal forces that are carried into the axle nests by elongated links 44 and 45. Thus all of the transverse loads on FIG. 10 are contained within a floating force loop not connected to ground at any point. The center twist is through an actuator or bell crank connected to ground by support 34. The loading for the center twist is applied through ledges or flanges on the bolster into the side frame 10 and out through the four bar links at the axle nests returning to ground at these points.

The bell crank loading members keep the machine compact. The end twist applied through actuators 100 and 101 which rock the evener beam about the longitudinal axis of the bolster apply a torque without affecting vertical load. One actuator retracts the same amount as the other extends. The end twist load is carried through the axle nests into the side frame 10 and this input is grounded only in torque, not position. The actuators 100 and 101 are mounted on swivel mountings to permit the actuator to swivel and keep the inputs precisely in torque without adding side loads.

The longitudinal input using actuator 115 provides equalized loads on the elongated links 44 and 45 and through the axle nests. This also is an ungrounded force loop.

By grounding only the major forces, vertical, center twist, and, if desired, end twist, and having the transverse input, and longitudinal input in ungrounded force loops, cross talk is minimized for ease of control and the test frame, actuators and controls can be kept compact, efficient and at a reasonable cost.

The outer end of bolster 40 may be supported by having it rest on an inflated air bag 50 (schematically shown in FIG. 7) that is mounted on a pedestal 50A on the frame 25. The support establishes a twist center but does not affect loading of the bolster. A radius rod having spherical rod ends extending between the end of bolster 40 and beam 30 also may be used for support if desired because it would let the bolster move without restraint in the loading directions.

What is claimed is:

1. A test apparatus for testing side frames of railroad cars, said side frames having a longitudinal center plane and having axle support means at opposite ends thereof, and having a center bolster support used for connecting a side frame to a railroad car on which the side frame is used, said test apparatus comprising a test frame member, said test frame member including a pair of first supports, separate hub means mounted in each of the axle support means of a side frame to be tested, each of said separate hub means being mounted on one of said first supports, linkage means to connect the respective hub means to each separate first support, the linkage means forming a separate four bar linkage with each hub means and the respective first support, each of said linkage means including a pair of links, first ends of the links of each pair being pivotally mounted to each respective first support on the test frame about first axes generally parallel to the longitudinal center plane of a side frame mounted on the hub means, and second ends of the links of each pair inclining toward each other in direction toward the respective hub means and being pivotally mounted at second ends thereof about second axes to the respective hub means, the lines extending between the first and second axes of the links of each pair intersecting at a point on the respective hub means pair lying substantially on the longitudinal center plane of a side frame mounted on the hub means and forming the instantaneous center of the respective four bar linkage formed, the instantaneous centers being rotationally free, and means to apply a force to a side frame mounted on said hub means adjacent the center bolster support of a side frame mounted on said hub means in direction generally parallel to the longitudinal center plane of a side frame mounted on the hub means causing a reaction resisted by said hub means and said linkage means.

2. The apparatus as specified in claim 1 wherein said center bolster support of a side frame mounted on the hub means comprises an opening having edges, and said means to apply a force to such side frame comprising a C shaped member having one leg protruding into the opening of such side frame and applying load on an edge defining said opening an equal amount on opposite sides of the longitudinal center plane of a side frame mounted on the hub means, said C-shaped member having a second leg generally parallel to the first leg and on the exterior of a side frame mounted on the hub means, the means to apply force further including an actuator connected to said lower leg to apply the force generally along a line lying along the longitudinal center plane of a side frame mounted on the hub means.

3. The apparatus as specified in claim 2 wherein said means to apply force includes a bell crank member having a bell crank pivot positioned laterally of the longitudinal center plane of a side frame mounted on the hub means, said bell crank having first and second legs, a first of said legs having a pivot connection lying generally along the longitudinal center plane of the side frame mounted on the hub means, a link extending between said pivot connection of the bell crank and said second leg of said C shaped member, and said actuator means applying force to said second leg of the bell crank.

4. The combination as specified in claim 1 and a pair of elongated links, one elongated link being connected to each of the hub means, said elongated links extending generally parallel to each other and perpendicular to the plane of a side frame mounted on the hub means, an evener member pivotally connected to the outer ends of said elongated links at a location spaced laterally from the longitudinal center plane of a side frame mounted on the hub means, said hub means having means to react forces to a side frame mounted on the hub means in directions perpendicular to the longitudinal center plane of such side frame, and second means to apply a force between the evener member and a side frame mounted on the hub means, said second means to apply force being positioned between said elongated links.

5. The apparatus of claim 4 wherein the second means to apply force includes a member having means for mounting it in the center bolster support of a side frame mounted on the hub means.

6. The combination as specified in claim 4 and loading means mounted within the space defined by the elongated links and evener member operable between the beam member and each of said elongated links to simultaneously load a first of said elongated links away from said beam member and a second of said elongated links toward said beam member.

7. The combination as specified in claim 6 wherein said loading means includes a lever pivotally mounted on said beam member about a lever pivot axis generally parallel to the plane of a side frame mounted on said hub means, an actuator acting between a first of said elongated links and said lever on a first side of the lever pivot axis, and link means mounted on said lever on an opposite side of the lever pivot axis from said actuator, and connected to the other of said elongated links.

8. The apparatus as specified in claim 1 wherein said means mounted in the center bolster support on a side frame mounted on the hub means comprises a longitudinally elongated beam member extending generally normal to the longitudinal center plane of a side frame mounted on the hub means, an evener member pivotally mounted to said beam member to permit slidable movement longitudinally along the beam member, a pair of elongated links having outer ends, said elongated links being generally parallel to each other and to the beam member and being connected to the hub means, respectively, said evener member being pivotally mounted to the outer ends of each of said elongated links, and an actuator member mounted to said beam member generally along the center line of said beam member and adapted to apply force to said evener member tending to move said evener member along the center line of said beam member thereby loading each of said elongated links along its longitudinal axis, said hub means and said beam member each having means to restrain longitudinal movement thereof relative to a side frame mounted on the hub means, whereby such side frame is loaded in direction transverse to its longitudinal center plane in a closed force loop between its axle support means and the center bolster support.

9. The apparatus as specified in claim 8 and an actuator member mounted at one end relative to said test frame and positioned laterally of said beam member and having an opposite end, means connected between said opposite end and said beam member exerting a force tending to move the outer end of said beam member and said evener member in direction laterally relative to said beam member and thereby to tend to twist the beam member relative to a side frame mounted on the hub means, said beam member including means to react loads from the actuator to a side frame mounted on the hub means and such loads being further reacted to the test frame member through said hub means and linkage means.

10. The combination as specified in claim 8 and second actuator means mounted on said test frame member at locations spaced outwardly from the longitudinal axis of said beam member, and operable to twist said beam member about its longitudinal axis, said second actuator means applying the twist actuable along lines of force generally parallel to the longitudinal center plane of a side frame being tested.

11. The combination as specified in claim 8 wherein said means to apply a force comprises a bell crank, an actuator having a first end thereof connected to operate said bell crank, said test frame member including a backbone member extending generally parallel to and below the beam, an opposite end of said actuator being mounted on said backbone member below said beam.

12. A testing apparatus for testing a side frame for a railroad car, said side frame comprising an elongated member having a longitudinal center plane and having a separate axle support nest at each of the opposite ends thereof, and means for connecting the side frame to a railroad car on which the side frame is used, said test apparatus comprising a test frame member having a primary loading plane, said test frame member including a base, hub means adapted to be received in the axle nests of a test side frame to support such a test side frame with the longitudinal center plane of such test side frame coinciding with the primary loading plane, linkage means to support each hub means with respect to said base, said linkage means carrying loads applied in a first direction parallel to the primary loading plane and perpendicular to a line extending between the centers of said hub means and permitting limited movement transverse to the primary loading plane, first loading means connected to said base and having coupling means adapted to be connected to a test side frame mounted on the hub means and operable to apply a load to said test side frame in the first direction, separate elongated link means connected to each of the hub means and extending transverse to the primary loading plane, an evener beam pivotally extending between and being connected to the separate elongated link means at locations thereon spaced from the hub means, and second loading means connected to said evener beam at a location between the separate elongated link means and being adapted to react loads to a test side frame mounted on said hub means in direction generally normal to the primary loading plane, said second loading means being actuable to apply tension loads to said elongated link means through said evener beam, said hub means including means to react loads on the separate elongated link means to a test side frame mounted on said hub means.

13. The apparatus of claim 12 wherein the linkage supporting each hub means comprises at least one pair of links, first ends of the links being pivotally mounted about spaced parallel first axes with respect to said base and second ends of the links inclining toward each other and being pivotally mounted at second ends about spaced generally parallel second axes to the hub means, the first and second axes also being generally parallel to each other and the lines between the first and second axes of the respective links intersecting at a point lying on the primary loading plane.

14. The apparatus of claim 12 wherein the means for connecting a test side frame to a railway car comprises an opening in the center portions thereof having load carrying edges, one edge of the opening carrying the load from the first loading means, and wherein said first loading means comprises a C shaped member having first and second spaced legs extending transverse to the primary loading plane, the first leg passing into the opening of a test side frame mounted on the hub means, the second leg being positioned on the exterior of a test side frame, and load applying means exerting a force on the second leg generally along a line centered on said primary loading plane.

15. The apparatus of claim 12 wherein the opening in the center portions of a side frame mounted on the hub means has peripheral edges, a bolster beam mounted in the opening and extending generally parallel to the elongated link means, said second loading means being mounted on the bolster beam to react loads to a test side frame through the bolster beam.

16. The apparatus of claim 15 and third loading means mounted with respect to said test frame and coupled to the bolster beam and to apply a load to the bolster beam in a plane generally mutually perpendicular to the primary loading plane and the first direction.

17. The apparatus of claim 15 further comprising actuator means connected to the evener beam on opposite sides of the second loading means and to the base, said actuator means being operable to apply a couple load to the evener beam about the axis of loading of the second loading means.

* * * * *